United States Patent
Hermann et al.

[11] Patent Number: 5,944,734
[45] Date of Patent: Aug. 31, 1999

[54] BALLOON DISSECTING INSTRUMENTS

[75] Inventors: George D. Hermann, Portola Valley; Fred H. Co, Santa Clara; Douglas S. Sutton, Pacifica, all of Calif.

[73] Assignee: General Surgical Innovations, Inc., Palo Alto, Calif.

[21] Appl. No.: 08/960,793

[22] Filed: Oct. 30, 1997

Related U.S. Application Data

[63] Continuation of application No. 08/688,044, Jul. 29, 1996, abandoned, which is a continuation-in-part of application No. 08/447,124, May 22, 1995, Pat. No. 5,702,417.

[51] Int. Cl.$^6$ .................................................. A61M 29/00
[52] U.S. Cl. ......................... 606/192; 606/108; 606/190
[58] Field of Search .................................. 606/190, 194, 606/198, 108, 195; 604/96

[56] References Cited

U.S. PATENT DOCUMENTS

| | | | |
|---|---|---|---|
| 4,312,353 | 1/1982 | Shahbabian | 128/344 |
| 4,493,711 | 1/1985 | Chin et al. | 604/271 |
| 4,779,611 | 10/1988 | Grooters et al. | 128/4 |
| 4,932,959 | 6/1990 | Horzewski et al. | 606/194 |
| 5,032,113 | 7/1991 | Burns | 604/96 |
| 5,183,463 | 2/1993 | Debbas | 604/98 |
| 5,188,630 | 2/1993 | Christoudias | 606/1 |
| 5,197,971 | 3/1993 | Bonutti | 606/192 |
| 5,269,753 | 12/1993 | Wilk | 604/49 |
| 5,307,814 | 5/1994 | Kressel et al. | 128/653.5 |
| 5,331,975 | 7/1994 | Bonutti | 128/898 |
| 5,346,504 | 9/1994 | Ortiz et al. | 606/192 |
| 5,359,995 | 11/1994 | Sewell, Jr. | 128/20 |
| 5,373,840 | 12/1994 | Knighton | 128/4 |
| 5,383,889 | 1/1995 | Warner et al. | 606/192 |
| 5,391,178 | 2/1995 | Yapor | 606/192 |
| 5,425,357 | 6/1995 | Moll et al. | 128/20 |
| 5,454,365 | 10/1995 | Bonutti | 600/204 |
| 5,458,639 | 10/1995 | Tsukashima et al. | 604/96 |
| 5,496,276 | 3/1996 | Wang et al. | 606/194 |
| 5,496,345 | 3/1996 | Kieturakis et al. | 606/192 |
| 5,514,153 | 5/1996 | Bonutti | 606/190 |
| 5,601,589 | 2/1997 | Fogarty et al. | 606/192 |
| 5,607,441 | 3/1997 | Sierocuk et al. | 604/96 |
| 5,762,604 | 6/1998 | Kieturakis | 606/190 |

FOREIGN PATENT DOCUMENTS 0411767  8/1991  France.

Primary Examiner—Michael Buiz
Assistant Examiner—Kevin Truong
Attorney, Agent, or Firm—Lyon & Lyon LLP

[57] ABSTRACT

Balloon loaded dissection devices with elongate balloons and a pushing member are disclosed for creating a tunnel alongside an elongate vessel in the body. The devices may utilize an elongate balloon of any suitable length which may be formed of an elastic or non-elastic material. The balloon may be of double walled construction and may be provided with a central lumen which may receive a guide rod, scope or other surgical instrument. The device may have a support tube secured to the inner wall of the balloon to provide columnar support for the apparatus. The support tube receives the guide rod, scope or other surgical instrument and may have a stop member to translate pushing force applied to the guide rod or scope to pushing force on the apparatus. By using the guide rod or scope as a pushing member the apparatus may be advanced alongside the vessel it is desired to dissect free from attached tissue. A balloon cover which may be elastic or resilient is provided to surround the balloon and facilitate compression of the balloon after it is deflated.

20 Claims, 8 Drawing Sheets

5,944,734

BALLOON DISSECTING INSTRUMENTS

CROSS REFERENCE TO RELATED APPLICATIONS

This is a continuation of U.S. application Ser. No. 08/688,044, filed on Jul. 29, 1996, now abandoned which is a continuation-in-part of U.S. application Ser. No. 08/447,124, filed on May 22, 1995 now U.S. Pat. No. 5,702,417. The priority of these prior applications are expressly claimed and their disclosure are hereby incorporated by reference in their entirety.

FIELD OF THE INVENTION

This invention relates to methods and devices for endoscopic vascular surgery, in particular to methods and devices for dissecting tissue to create a working space adjacent a blood vessel.

BACKGROUND OF THE INVENTION

Numerous surgical procedures have been developed to replace arteries that have become blocked by disease. The aortocoronary bypass surgery is perhaps the most important of these bypass operations. The coronary arteries supply blood to the heart. As a result of aging and disease, coronary arteries may become blocked by plaque deposits, stenosis, or cholesterol. In some instances, these blockages can be treated with atherectomy, angioplasty or stent placement, and coronary bypass surgery is not required. Coronary bypass surgery is required when these other methods of treatment cannot be used or have failed to clear the blocked artery. In coronary bypass surgery, a vein is harvested from elsewhere in the body and grafted into place between the aorta and the coronary artery below the point of blockage. An illustration of this surgery is shown in FIG. 1, which shows the heart 1 and the right anterior coronary artery 2 and the left anterior coronary artery 3 which supply blood to the heart. The right anterior coronary artery 2 is blocked in its proximal segment at 2a, as shown. This blockage has been bypassed by grafting a segment of vein 4 between the aorta 5 and the distal segment 2b of the right anterior coronary artery 2. Similarly, the left anterior coronary artery 3 may be blocked, and may require bypass with a length of vein 4a between the aorta and the distal segment 3b of the left anterior artery. The operation requires access to the heart, which means that the chest cavity must be opened completely.

The coronary bypass surgery requires a length of vein or artery for the graft. It is preferred to use a vein taken from the patient undergoing the bypass surgery. The patient is a ready source of suitable veins that will not be rejected by the body after transplantation and grafting onto the aorta and coronary artery. The saphenous vein in the leg is the best substitute for small arteries such as the coronary arteries, and it is the preferred vein for use in coronary bypass surgery. This is because the saphenous vein is typically 3 to 5 mm in diameter, about the same size as the coronary arteries. Also, the venous system of the legs is sufficiently redundant so that after removal of the saphenous vein, other veins that remain in the leg are adequate to provide return blood flow. The cephalic vein in the arm is an alternative that is sometimes used.

A typical operation previously required to harvest the saphenous vein is illustrated in FIG. 2. The surgeon cuts into the leg to allow access to the saphenous vein and cuts the vein from the leg. To expose the saphenous vein 6, the surgeon makes a series of incisions from the groin 7 to the knee 8 or the ankle 9, leaving a one or more skin bridges 10 along the line of the incisions. Some surgeons make one continuous incision from the groin to the knee or ankle. Handling of the vein must be kept to a minimum, but the vein must be dissected free from connective tissue. After exposing the vein, the surgeon grasps it with his fingers while stripping off the surrounding tissues with dissecting scissors or other scraping instruments. The surgeon uses his fingers and blunt dissection tools to pull and lift (or mobilize) the vein from the surrounding tissue. The vein is mobilized or pulled as far as possible through each incision. To reach under the skin bridges, the surgeon lifts the skin with retractors and digs the vein free. While stripping the vein, the surgeon will encounter the various tributary veins that feed into the saphenous vein. These tributaries must be ligated and divided. To divide and ligate tributaries that lie under the skin bridges, the surgeon may need to cut one end of the saphenous vein and pull it under the skin bridge to gently pull the vein out from under the skin bridge until the tributary is sufficiently exposed so that it may be ligated and divided. When the vein has been completely mobilized, the surgeon cuts the proximal and distal ends of the vein and removes the vein from the leg. After removal, the vein is prepared for implantation into the graft site, and the long incisions made in the leg are stitched closed.

The procedure described above can be used to harvest veins for a femoral popliteal bypass, in which an occluded femoral artery is bypassed from above the occlusion to the popliteal artery near the level of the knee. The procedure can also be used to harvest veins for the revascularization of the superior mesenteric artery which supplies blood to the abdominal cavity and intestines. In this case, the harvested vein is inserted between the aorta to the distal and patent (unblocked) section of the mesenteric artery. For bypass grafts of the lower popliteal branches in the calf, the procedure can be used to harvest the umbilical vein. The harvested vein can also be used for a vein loop in the arm (for dialysis) between the cephalic vein and brachial artery.

As can be seen from the description above, the vein harvesting operation is very traumatic in its own right. In the case of coronary artery bypass, this operation is carried out immediately before the open chest operation required to graft the harvested vein into the coronary arteries. The vein harvesting operation is often the most troublesome part of the operation. The long incisions created in the leg can be slow to heal and very painful. Complications resulting from the vein harvesting operation can also hinder the patient's recovery from the entire operation.

The method of vein harvesting presented herein is accomplished with laparoscopic procedures. This allows the veins to be harvested in an operation that requires only a few small incisions. Endoscopic surgical techniques for operations such as gall bladder removal and hernia repair are now common. The surgeon performing the operation makes a few small incisions and inserts long tools, including forceps, scissors, and staplers, into the incision and deep into the body. Viewing the tools through a laparoscope or a video display from the laparoscope, the surgeon can perform a wide variety or maneuvers, including cutting and suturing operations, necessary for a wide variety of surgical procedures and operations.

Minimally invasive procedures for vein removal have been proposed. U.S. Pat. No. 5,373,840 to Knighton, entitled, "Endoscope and Method for Vein Removal," shows a method of cutting the saphenous vein at one end, and grasping the vein with graspers or forceps, then sliding a ring over the vein while holding it. Knighton uses a dissecting tool with an annular cutting ring, and requires that the saphenous vein be overrun or progressively surrounded with the dissecting tool and the endoscope, so that after the endoscope has been inserted as far as it will go, the entire dissected portion of the vein has been pulled into the lumen of the endoscope. As shown in FIGS. 1 and 10 of Knighton, the method requires deployment of forceps inside the annular dissection loop, and it requires deployment of the loop and graspers inside the endoscope lumen. The blood vessel must be cut and grasped by the forceps before it can be dissected by the dissecting ring.

SUMMARY OF THE INVENTION

The methods and devices disclosed herein allow surgeons to harvest veins, or dissect along other elongate structures without making long incisions through the skin to access the structure as previously required. The present devices permit minimally invasive procedures which, in the case of a saphenous vein harvest, require just two small incisions, one at either end of the saphenous vein, to be performed. The procedure is accomplished with laparoscopic instruments under the guidance of a laparoscope.

In a first preferred embodiment, a blunt loaded balloon dissector has an elongate balloon of any suitable length which may be formed of an elastic or non-elastic material. The balloon may be of double walled construction and may be provided with a central lumen which may receive a guide rod, scope or other surgical instrument. The device may have a support tube secured to the inner wall of the balloon to provide columnar support for the apparatus. The support tube receives the guide rod, scope or other surgical instrument and may have a stop member to translate pushing force applied to the guide rod or scope to pushing force on the apparatus. By using the guide rod or scope as a pushing member the apparatus may be advanced alongside the vessel it is desired to dissect free from attached tissue. A balloon cover which may be elastic or resilient is provided to surround the balloon and facilitate compression of the balloon after it is deflated.

In another embodiment of the invention, another pushable balloon dissection device is provided which also may utilize an elongate balloon. The balloon in this embodiment may have a central lumen to receive a scope or other laparoscopic instrument. The apparatus has a guide tube which receives a guide rod with a slender metal rod and enlarged tip. The guide rod is utilized as a pushing member. A resilient balloon cover may also be provided in this embodiment to compress the balloon upon deflation.

In yet another preferred embodiment of the invention, a pushable balloon dissection apparatus may have an elongate balloon disposed over an elongate shaft or tubular member such that the shaft or tubular member resides within the interior space of the balloon. The balloon dissector may be advanced between the tissue planes it is desired to dissect and then inflated to create a tunnel alongside a vessel or other elongate structure. The balloon may then be serially deflated, further advanced and reinflated to enlarge the tunnel. When the apparatus is provided with a tubular member, a laparoscope may be inserted into the bore of the tubular member and utilized as a pushing member to advance the apparatus and to provide observation of the procedure. A resilient balloon cover may also be utilized in this embodiment to assist in deflating and compressing the balloon to facilitate redeployment of the apparatus.

The method of vein harvesting disclosed herein utilizes an elongate tubular balloon to dissect a tunnel alongside the vein to be harvested. The elongate balloon may be wrapped around a guide rod or endoscope and inserted through a small incision in the leg and pushed along the vein to create a small tunnel over the vein. The elongate balloon may be provided with a balloon cover which may be a separate removable cover or attached to the balloon. When the balloon is in place adjacent the vein to be dissected, the removable balloon cover (if provided) may be removed and the balloon inflated to enlarge the tunnel and create a working space for insertion of endoscopic instruments. The guide rod or endoscope may be removed to allow other endoscopic instruments to be passed into the tunnel through the balloon.

In a preferred method of harvesting the saphenous vein, the surgeon makes one small incision at each end of the saphenous vein. After making the incisions, the surgeon inserts a tunneling instrument or blunt dissector which carries a long balloon into one incision and advances or pushes the dissector along the saphenous vein to make a small tunnel along the saphenous vein. The surgeon then inflates the long balloon to enlarge the tunnel. When the tunnel is enlarged to an appropriate size, the surgeon removes the balloon and seals the tunnel at both ends. The surgeon may then injects carbon dioxide into the tunnel at sufficient pressure (typically 5–15 mm Hg) to inflate the tunnel and create room for laparoscopic instruments. The surgeon then inserts a laparoscope through the seal to provide a view of the procedure, and inserts a laparoscopic vein harvesting device, such as one of the hooked vein harvesting devices disclosed in copending U.S. application Ser. No. 08/444,424 entitled, "Methods and Devices for Blood Vessel Harvesting," into the leg to dissect the connective tissue from the vein, identify side branches, and remove the vein from the leg. The disclosure of the aforementioned application Ser. No. 08/444,424 is hereby incorporated by reference in its entirety. After the vein is loosened or dissected free from its channel in the leg, the surgeon can cut the proximal and distal ends of the vein and easily pull the vein from the leg. The small skin incisions are then stitched so that they may heal. The small incisions heal much more readily, with fewer complications and far less pain, than the open procedures now in use.

DETAILED DESCRIPTION OF A PREFERRED EMBODIMENT

Figure 4:
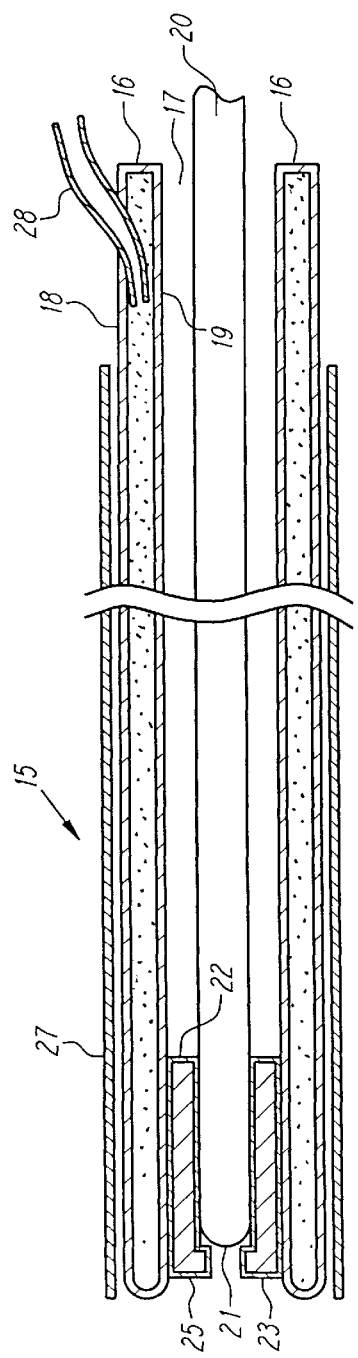
FIG. 4 shows a balloon dissector according to the invention uninflated and ready for insertion.

FIG. 4 shows an embodiment of a balloon loaded blunt dissector 15 in its uninflated state, with a balloon 16 packed inside the device. The balloon 16 is a nonelastic balloon or bladder and is cylindrical or tubular with a central lumen 17. The balloon 16 has two walls 18 and 19 and may be described as a double walled balloon tube. The balloon 16 may be made of polyethylene, polyurethane, polyamide and other nonelastic materials as well as latex and other elastic materials. The balloon 16 may be any suitable length, for example 12 to 24 inches long, to provide of a tunnel of convenient length when harvesting the saphenous vein. The balloon 16 may be any convenient diameter or width, for example 2 to 3 inches, to allow laparoscopic instruments to fit and operate conveniently within the tunnel created by the balloon 16. The balloon tube 16 may have any suitable cross-sectional shape.

Figure 5:
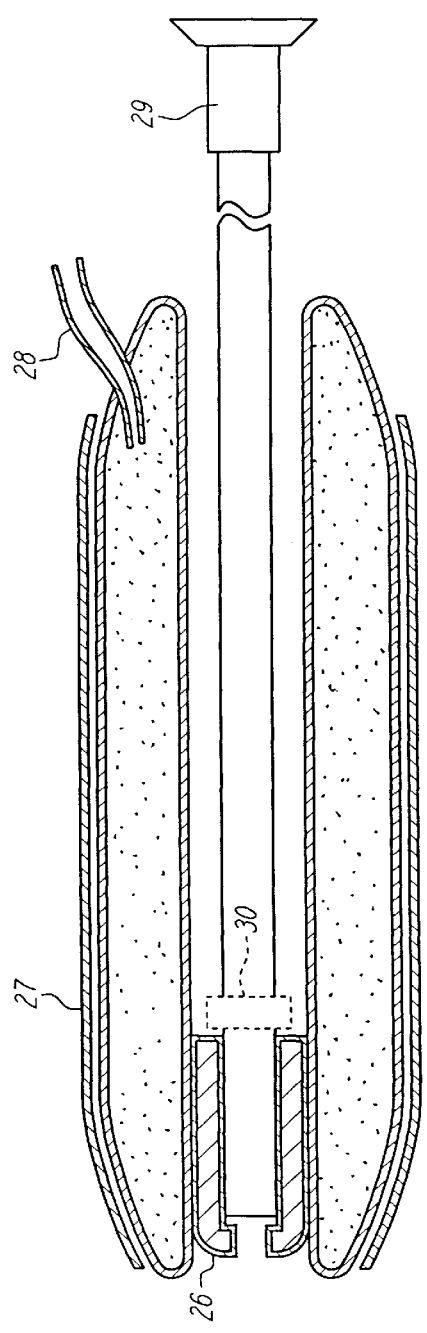
FIG. 5 shows a balloon dissector according to the invention in its inflated state.

A guide rod 20 with a blunt or rounded tip 21 is disposed in the central lumen 17 of the double walled balloon tube 16. The guide rod 20 is used as a pushing member to push the balloon 16 through body tissue. A support tube 22 may be provided to give some columnar support to the device and provide a stop member or coupling member to translate pushing force applied to the guide rod 20 to pushing action on the balloon tube 16. The support tube 22 may be secured to the inner wall of the balloon tube 16 in any suitable fashion. The support tube 22 may have an overhanging lip 23 which obstructs passage of the guide rod 20 or endoscope 29 (if provided). Alternatively, the guide rod 20 or endoscope 29 can be fitted with a stop collar 30 to engage the support tube 22 (as shown in FIG. 5). The support tube 22 may have a square tip 25 as in FIG. 4 or a rounded tip 26 as shown in FIG. 5. The guide rod 20 and support tube 22 are used to push the balloon 16 along the saphenous vein or other desired pathway between tissue layers. Use of the support tube 22 permits the guide rod 20 or endoscope 29, if utilized as the pushing member, to be removably received by the apparatus 15. This allows the apparatus 15 to use fairly expensive and nondisposable devices such as the endoscope as the pushing member. If visualization is not needed or desired, the balloon 16 may be sealed to a disposable pushing member and may be coupled to the pushing member with adhesives, heat sealing or integral construction or any other coupling means. A balloon cover 27 surrounds the balloon tube 16 and provides a protective sheath during placement of the balloon loaded dissector 15. The balloon cover 27 may be a thin sheath of polyethylene or other plastic film, or it may be a more rigid tube of PVC, PTFE, PETG, polyethylene or other plastic.

The balloon cover 27 may be elastic or resilient so that it serves to compress the balloon 16, so that the balloon 16 quickly and automatically collapses upon deflation. The balloon cover 16 may be made resilient by choosing a resilient material such as a thin sheet of polyethylene which is sufficiently resilient and elastic under the pressure used to inflate the balloon 16. The balloon 16 itself may also be made of polyethylene, and may be a thick polyethylene which is nonelastomeric under range of pressure used to inflate the balloon 16. When the balloon 16 and balloon cover 27 are made of the same material or a miscible material, the balloon 16 may be heat sealed to the balloon cover 27 at various points to prevent the balloon cover 27 from inadvertently slipping off the balloon 16. When the balloon 16 and balloon cover 27 are made of different or immiscible materials, they may be attached with adhesive or through the use of other suitable fasteners.

Figure 1:
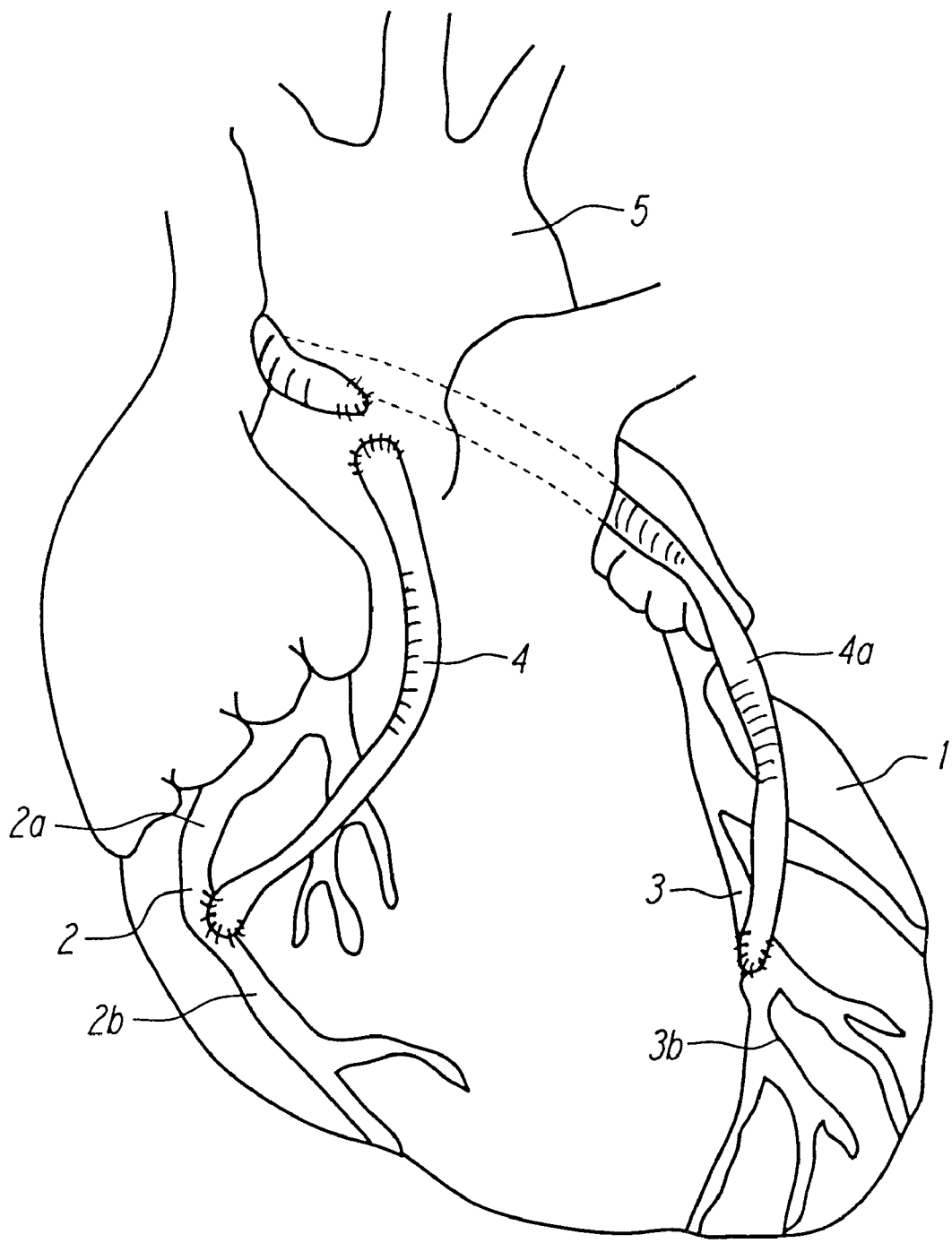
FIG. 1 is a front view of the heart showing a vein grafted from the aorta to the right anterior coronary artery, bypassing the proximal segment of the right anterior coronary artery.
Figures 2, 3:
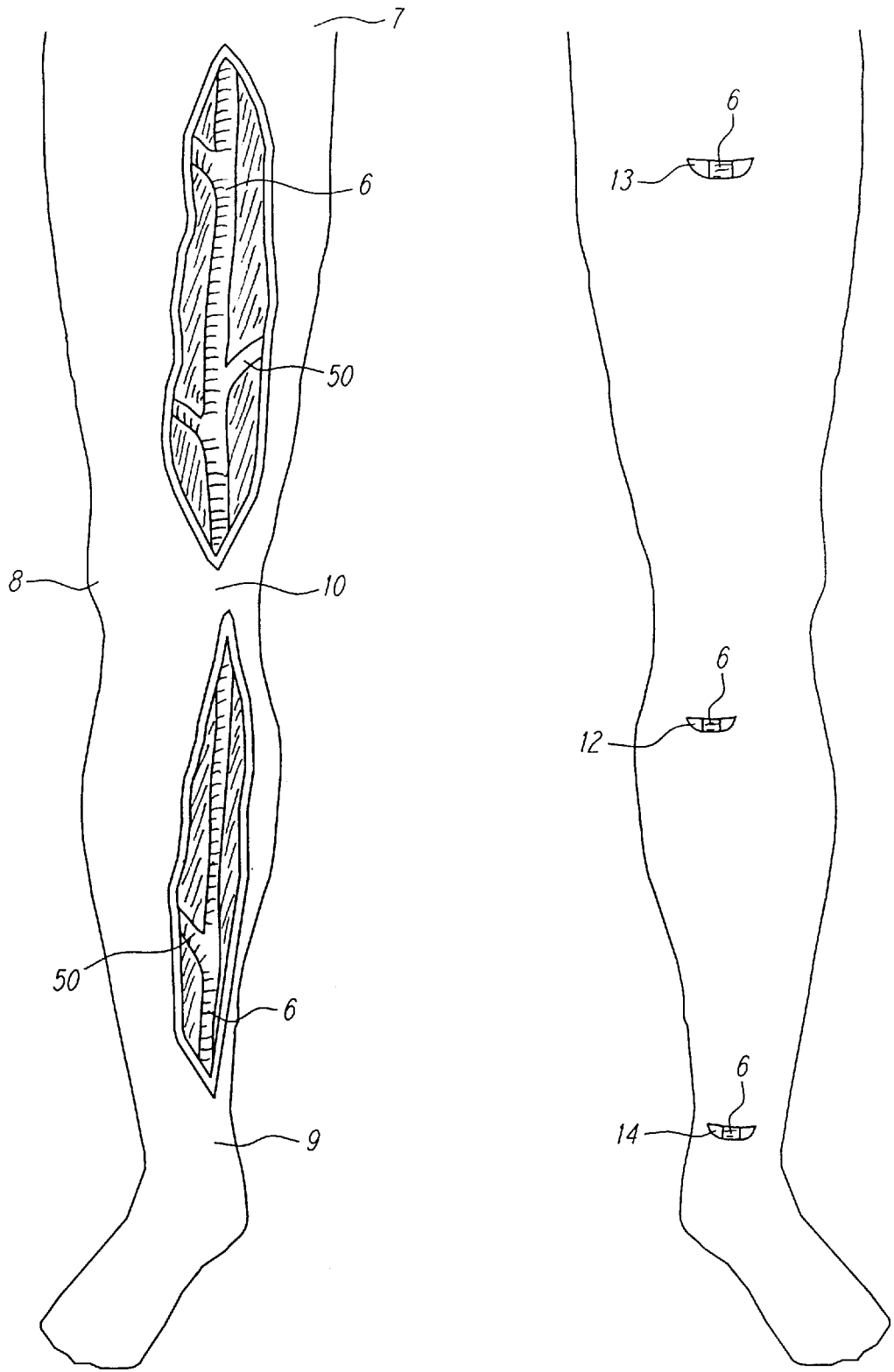
FIG. 2 is a view of the leg showing the incisions necessary for harvesting the saphenous vein using a traditional open procedure.
FIGS. 3, 3a and 3b are views of the leg showing the incisions necessary for harvesting the saphenous vein according to the methods presented herein.

In the preferred embodiment of a method of using the devices disclosed herein, the surgeon uses a balloon loaded dissector to create a working space under the skin and over the saphenous vein suitable for laparoscopic techniques. The surgeon makes one or more incisions as shown in FIG. 3, to expose the saphenous vein. These incisions are referred to as cut-downs. An incision at the knee 12, an incision at the groin 13, or an incision close to the ankle 14 can be used. In FIG. 3, the saphenous vein 6 can be seen through the cut-downs 12, 13 and 14. It will be apparent from the description that the use of three or four incisions to harvest the entire saphenous vein is merely a matter of convenience, and those particularly skilled in laparoscopic procedures may require fewer incisions, and smaller incisions than illustrated may be required.

After insertion, the balloon loaded blunt dissector 15 is pushed along the blood vessel until the balloon tube 16 is located over the desired length of the saphenous vein. When the balloon 16 is properly in place it occupies a narrow tunnel over the saphenous vein. When in place, the balloon 16 is inflated through inflation tube 28. As shown in FIG. 5, the outer walls expand under inflation and the balloon cover 27 stretches as the balloon 16 is inflated. The expansion of the balloon 16 enlarges the tunnel. The outer diameter of the balloon tube 16 defines the size of the tunnel that is created, and the outer diameter may be controlled during manufacture and during inflation. Also as shown in FIG. 5, the guide rod 20 may be conveniently replaced with an endoscope 29 which can also serve as the pushing member. The endoscope 29 can be chosen to have an outer diameter matching the support tube, or it can be provided with a stop collar 30, both constructions serving to couple the endoscope 29 to the balloon tube 16 so that pushing on the endoscope 29 serves to push the balloon 16 into the body.

When the balloon 16 is deflated through the inflation tube 28, the balloon cover 27 serves to compress and collapse the balloon 16 and squeeze the inflation fluid out of the balloon 16, thus returning the balloon 16 to the collapsed state shown in FIG. 4. After the balloon 16 has been collapsed by the elastic force of the balloon cover 27, the device 15 may be further advanced or pulled-back from its position in the body, and repositioned at another area of interest. When the balloon 16 is repositioned, it may be reinflated to enlarge the tunnel. The balloon 16 may be repeatedly inflated and deflated in this manner. Alternatively, the balloon cover 27 may be removed by pulling it proximally out of the incision to allow the balloon 16 to expand.

Figure 6:
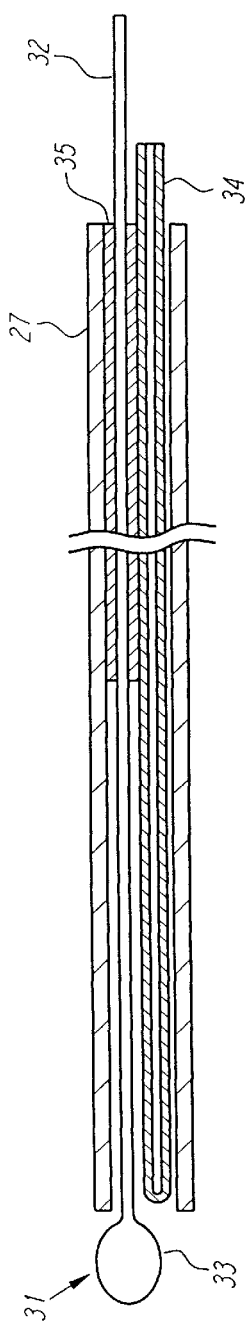
FIG. 6 is a cross-section of an alternate embodiment of a balloon dissector according to the invention in its uninflated state.

FIG. 6 shows an alternate embodiment of a balloon loaded blunt dissector. The guide rod 31 is provided with a slender metal rod 32 fitted with an enlarged tip or olive tip 33. The guide rod 31 may be replaced by a scope if visualization is desired. The balloon 34 is a long slender cylindrical balloon, with or without a central lumen. A guide tube 35 is attached to the outside of the balloon 34 and the guide rod 31 fits through the guide tube 35. The balloon 34 is uninflated in FIG. 6, and the balloon 34 and guide tube 35 are shown inside the balloon cover 27. The balloon 34 of FIG. 6 is used in the same way as the balloon 16 of FIGS. 4 and 5.

In operation, the apparatus is slipped over an endoscope (if utilized) or guide rod 31 and the balloon cover 27 is slipped over the apparatus. It is expected that use of an endoscope will be preferred, because it allows for visualization of the anatomy at its distal tip as the apparatus pushes through the fat layer overlying the saphenous vein. The apparatus is inserted either directly into the incision or is introduced through a cannula. After the guide rod 31 and balloon 34 are in place over the blood vessel, the balloon cover 27 can be pulled out of the incision, and may be provided with a weakened section to facilitate removal. The balloon cover 27 may be pulled back gradually as the balloon 34 is inserted to uncover that portion of the balloon 34 which is inside the body, and the balloon 34 can be inflated to dissect a larger tunnel in the early stages of insertion. The balloon cover 27 may also be left in place and, if made of a resilient material, can be used to compress the balloon 34 after deflation to facilitate repositioning of the assembly.

Figures 3A, 3B:
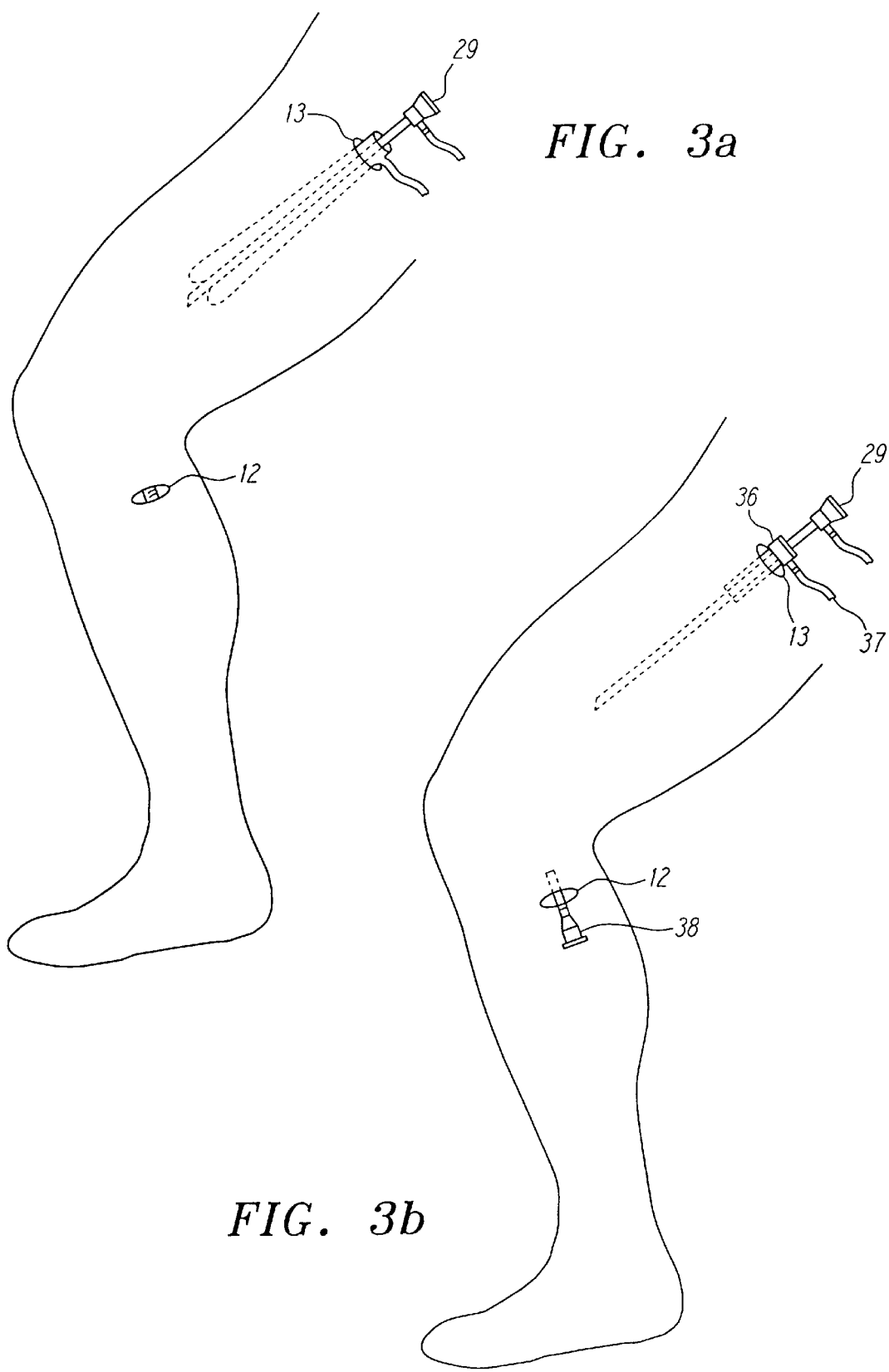

After full insertion, in a preferred method of use, the balloon 34 may be left in place in the tunnel while the endoscope is utilized to view the interior surfaces of the body at the tip of the apparatus, as shown in FIG. 3a. If the balloon 34 is provided with a central lumen, endoscopic instruments may be passed through said central lumen to perform surgical procedures on body parts such as the saphenous vein and communicating veins of the leg. In situations where it is desirable to insufflate the tunnel created by the balloon 34, the balloon 34 may be deflated and pulled out of the tunnel through cut-down 13, and a cannula port 36 with insufflation tube 37 may be inserted into the same cut-down as shown in FIG. 3b. A secondary endoscopic access port 38 may be inserted into the knee incision 12 to pass a variety of instruments into the work space.

The step of removing the balloon cover 27 may be avoided if the balloon cover 27 is perforated along a number of longitudinal lines and sealed to the balloon 34 along longitudinal lines, so that expansion of the balloon 34 tears the balloon cover 27 to allow expansion, but the pieces stay fixed to the balloon 34 so that they may be removed easily.

Figure 7:
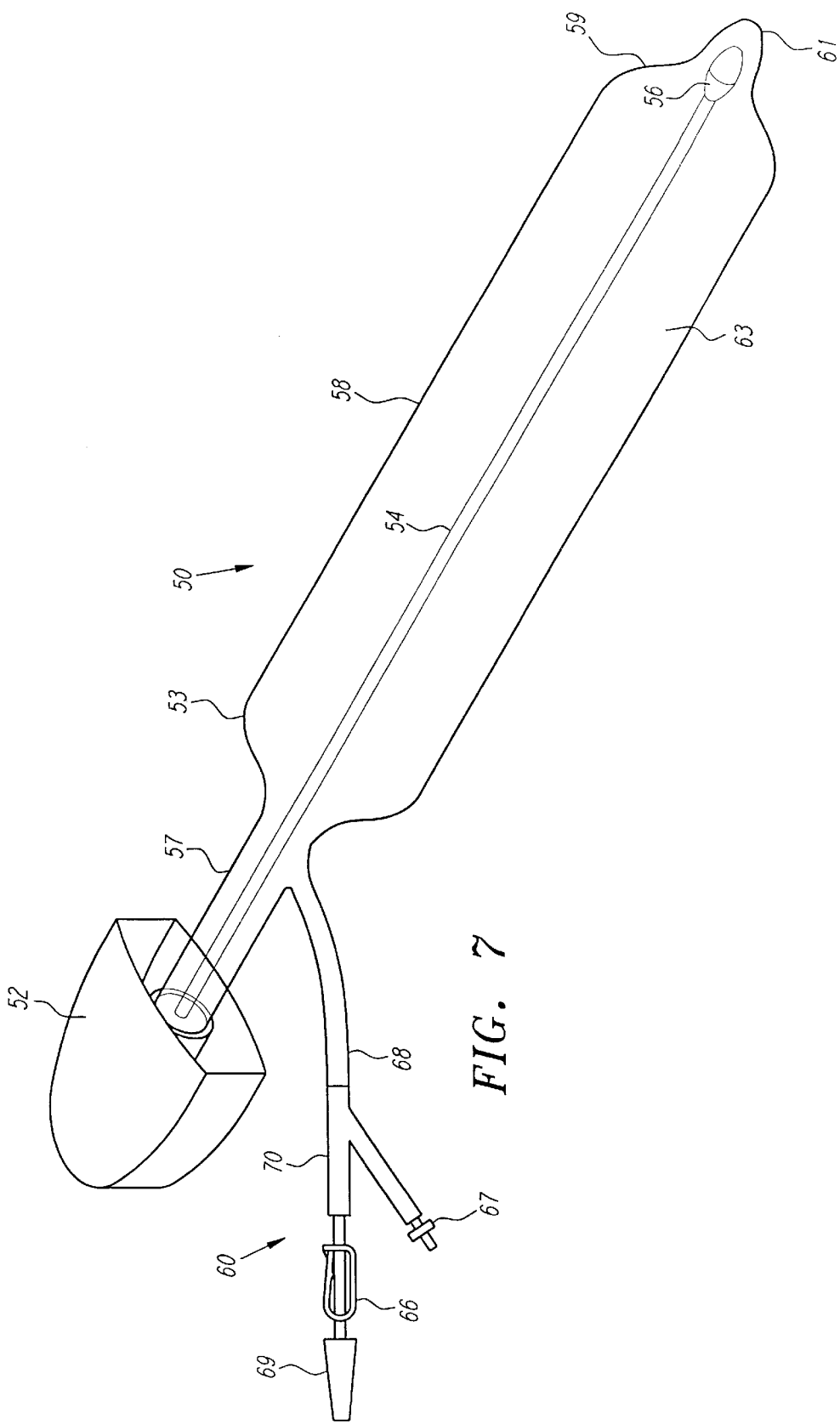
FIG. 7 is an isometric view of a balloon dissector according to the invention, illustrating the balloon dissector in its expanded state.

Another embodiment of a balloon dissection apparatus 50 is illustrated in FIG. 7. In this embodiment, the balloon dissector 50 includes a handle 52, a tunneling rod 54 which may be provided with a blunt tip 56, and an elongate balloon 58 having an inflation harness 60 extending from the balloon 58. The tunneling shaft 54 is formed of a suitable material such as surgical stainless steel to provide adequate rigidity for the shaft 54 to serve as a blunt obturator for tunneling between tissue layers. When the balloon dissector 50 is configured as an extraluminal balloon dissector to harvest the saphenous vein in the leg, for example, the tunneling shaft 54 may have a length of about 12 inches, and a diameter of approximately ⅛ inch. Alternatively, the tunneling shaft 54 may be formed from a semi-flexible material, such as plastic, for example, to accommodate situations where it is desirable to provide a tunneling shaft with the capability to navigate somewhat torturous passages within the body. The tunneling shaft 54 may be mounted in the handle 52 using any suitable fastening system, e.g., gluing or a compression fit. The blunt tip 56, which may be integrally formed with the tunneling shaft 54 or a separate member, provides a blunt distal end on the tunneling shaft 54. Although an olive-shaped tip 56 is illustrated, other shapes providing a blunt surface are possible. The blunt tip 56 may also be omitted.

The elongate balloon 58 has distal and proximal ends 59 and 53 and a neck portion 57 extending from the proximal end 53 of the balloon 58. For the purposes of this application, an elongate balloon is defined as a balloon having an axial length substantially greater than its transverse diameter when the balloon is inflated. As illustrated in FIG. 7, the elongate balloon 58 is mounted over the tunneling shaft 54 such that the tunneling shaft 54 lies within the interior space 63 of the balloon 58. The distal end 59 of the balloon 58 is preferably provided with a nipple or pocket 61 that may mate against the distal tip 56 of the tunneling shaft 54 to help protect against stretching or tearing of the distal tip of the balloon during tunneling. As will be described below, this construction permits the tunneling shaft 54 to be used as a pushing member to advance the deflated balloon 58 alongside a blood vessel or other elongate structure it is desired to dissect free of connected tissues.

The neck portion 57 of the balloon 58 may be secured inside the handle 52 in a fluid-tight fashion. Alternatively, the neck portion 57 may be secured to the tunneling shaft 54 by any suitable bonding system such as gluing or clamping. When the neck portion 57 is mounted in the handle 52 as illustrated in FIG. 7, the balloon inflation harness 60 may extend from the neck portion of the elongate balloon 57 to provide a fluid passageway into the interior space 63 of the balloon 58.

One example of a suitable balloon inflation assembly is illustrated in FIG. 7 in the form of balloon inflation harness 60. Balloon inflation harness 60 includes a tube 68 which extends from the balloon 58 and is connected to a wye fitting 70. A luer-type fitting with check valve 67, is connected to one port of the wye fitting 70 and an evacuation fitting 69 is connected to the other port of the wye fitting 70. A pinch clamp 66 is provided to close off the fluid passageway from the wye fitting 70 to the evacuation fitting 69. The balloon inflation harness 60 illustrated is of the same type as described in copending application Ser. No. 08/570,766, filed on Dec. 12, 1995, the disclosure of which is hereby incorporated by reference in its entirety. Of course, numerous other suitable balloon inflation assemblies are possible.

In the FIG. 7 example, the elongate balloon 58 is inflated by closing the pinch clamp 66 and injecting a suitable inflation fluid, preferably saline solution, although other fluids such as air may be utilized instead, through the fitting 67 into the balloon inflation lumen 68, which is in communication with the interior space 63 of the balloon 58.

As one alternative to the balloon inflation harness 60, the handle 52 may be provided with an inflation port which is in communication with the proximal end of the neck portion 57 of the elongate balloon 58. In this alternative embodiment, inflation fluid is injected through the inflation port in the handle 52 directly into the neck portion 57 of the balloon 58.

The balloon 58 is preferably constructed of a medical grade nonelastomeric material of suitable type such as a polyurethane according to known fabrication techniques so as to have a predetermined elongate shape. Although all nonelastomeric materials exhibit some degree of elasticity, for the purposes of this application, a nonelastomeric material is one which remains substantially inelastic over the desired inflation pressure ranges utilized for the particular procedure. Although an elastomeric balloon may be utilized with the balloon dissector 50, it is preferable to use an inelastic balloon so that the expansion envelope of the balloon can be more precisely predicted. In contrast, an elastomeric balloon tends to inflate following the path of least tissue resistance and localized differences in tissue resistance may cause an undesirable aneurysm in the balloon leading to nonuniform dissection.

In a preferred method of use, an incision is made in the body proximate the elongate structure within the body it is desired to dissect free of connective tissue. The surgeon identifies the appropriate tissue planes dissection is desired to occur along and the balloon dissector 50 is inserted, either directly or with the aid of a cannula, through the incision into the body and advanced following the identified tissue planes. The surgeon uses the handle 52 and pushes the balloon dissector 50 as a blunt obturator following the tissue planes adjacent the elongate structure until a desired location for deployment of the dissector 50 is reached. As the dissector 50 is advanced within the body, its progress may be monitored through the skin by direct observation and/or manual palpation. Depending on the procedure, varying amounts of the overall length of the elongate balloon 58 may be disposed within the incision.

Once the desired location for dissection has been reached through blunt tunneling, the elongate balloon 58 may be inflated by closing the pinch clamp 66 and communicating an inflation fluid through the balloon inflation harness 60 into the interior space 63 of the balloon 58. As it inflates, the balloon 58 expands into the predetermined elongate shape and dissects tissue away from the elongate structure to create a tunnel alongside the elongate structure. After the tunnel has been created, the dissector 50 may be deflated by releasing the pinch clamp 66 and applying vacuum to the male evacuation fitting 69. After deflation, the dissector 50 may be removed from the body through the incision, or further advanced alongside the elongate structure and reinflated to enlarge the tunnel.

After the dissector has been removed from the body, a cannula and skin seal assembly of the type disclosed in application Ser. No. 08/570,766, for example, may be inserted into the incision and the skin seal advanced into the incision to create a substantially gas-tight seal with the incision. The space created by the balloon dissector 50 may then be insufflated by injecting an appropriate insufflation gas through a port provided on the cannula should an insufflated operating space be desired.

Use of the dissector 50 specifically contemplates multiple serial balloon dissections. The dissector 50 may be advanced into the body in stages along the identified natural tissue planes by repeatedly advancing and deploying the dissector 50 to dissect a tunnel of the desired length alongside the elongate structure. The process of advancing the dissector 50, inflating the balloon 58, and deflating the balloon 58 may be repeated in serial fashion until the desired tunnel has been created. In the embodiment of the balloon dissector 50 illustrated in FIG. 7, a vacuum may be drawn on the balloon 58 to deflate and contract the balloon 58 so that the dissector 50 can be repositioned and redeployed as needed.

Figure 8:
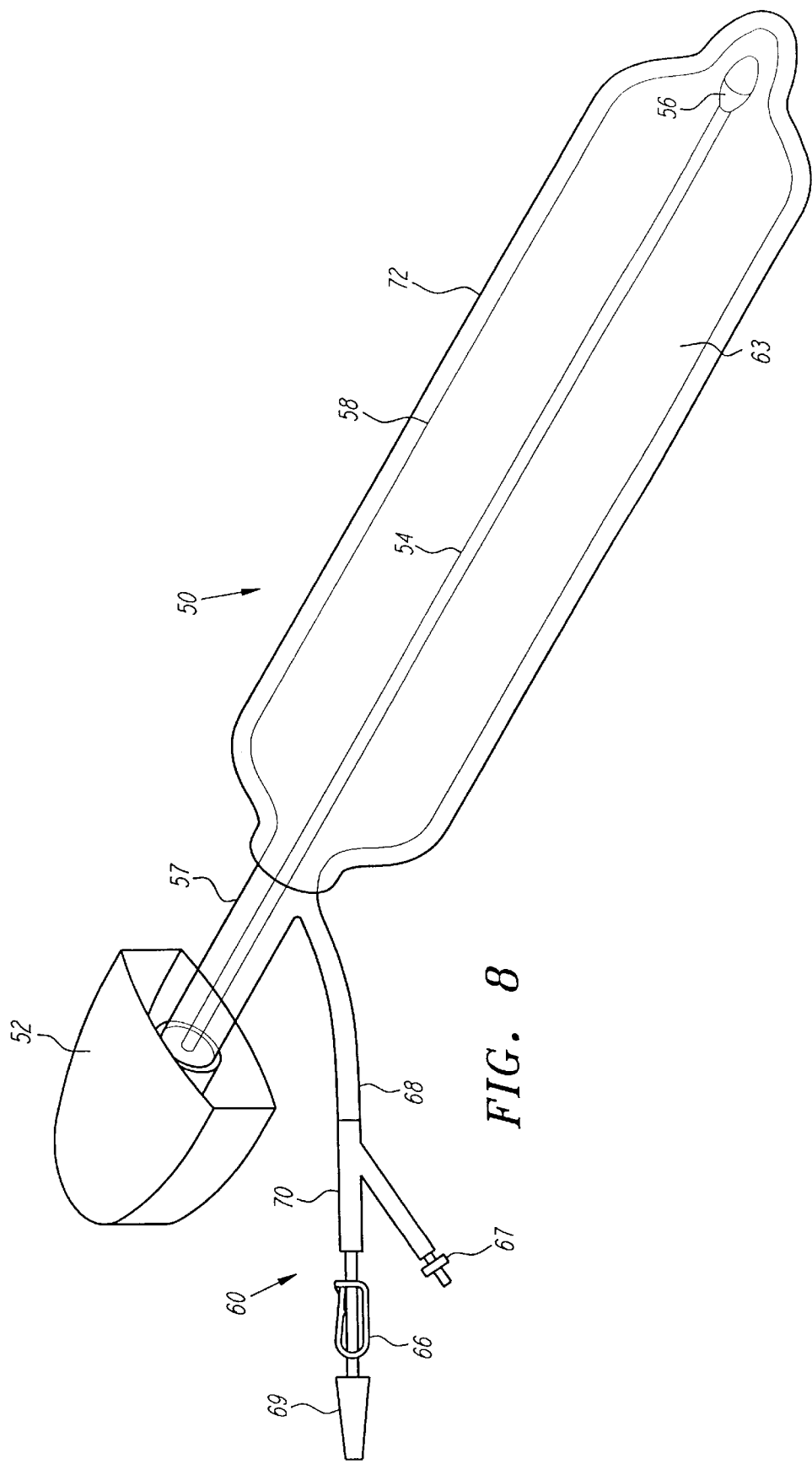
FIG. 8 is a view of the balloon dissector illustrated in FIG. 7 with a resilient balloon cover surrounding the elongate balloon.

The balloon dissector 50 is illustrated in FIG. 8 with an elastomeric balloon cover 72 that surrounds the elongate balloon 58. The dissector 50 is in all other respects identical to the FIG. 7 embodiment. The cover 72 preferably has a diameter such that when the balloon 58 is in a deflated condition, the cover 72 compresses the balloon 58 around the shaft 54. The use of the cover 72 thus aids in the serial redeployment of the balloon 58 by automatically causing the balloon to return to a compressed state upon deflation. The elastomeric cover 72 may be formed from a resilient material such as a thin sheet of polyurethane which is sufficiently resilient and elastic under the pressure used to inflate the balloon 58, or it may formed from an elastomer such as silicon or latex rubber.

The cover 72 may be bonded to the balloon 58 at various points using known bonding techniques to prevent the cover 72 from inadvertently slipping off the balloon 58. Alternatively, the cover 72 may have a diameter closely matching the diameter of the shaft 54 so that the cover 72 is retained in position by its elastic compression on the shaft 54, or by friction. The cover 72 may also completely cover the elongate balloon 58 and be secured in the handle 52. In this case, the cover 72 may be inflated independently of the elongate balloon 58 to provide a balloon with elastomeric characteristics, i.e., localized tissue expansion following the path of least tissue resistance.

As an alternative embodiment, the elongate balloon 58 may be elastic and the cover 72 may be inelastic such that the inelastic cover 72 acts to limit expansion of the elongate balloon 58.

It is also possible to utilize a separate removable cover of the type disclosed in copending application Ser. No. 08/570,766, for example, or an integral balloon cover which separates upon expansion of the balloon as described with reference to previous embodiments.

Figure 9:
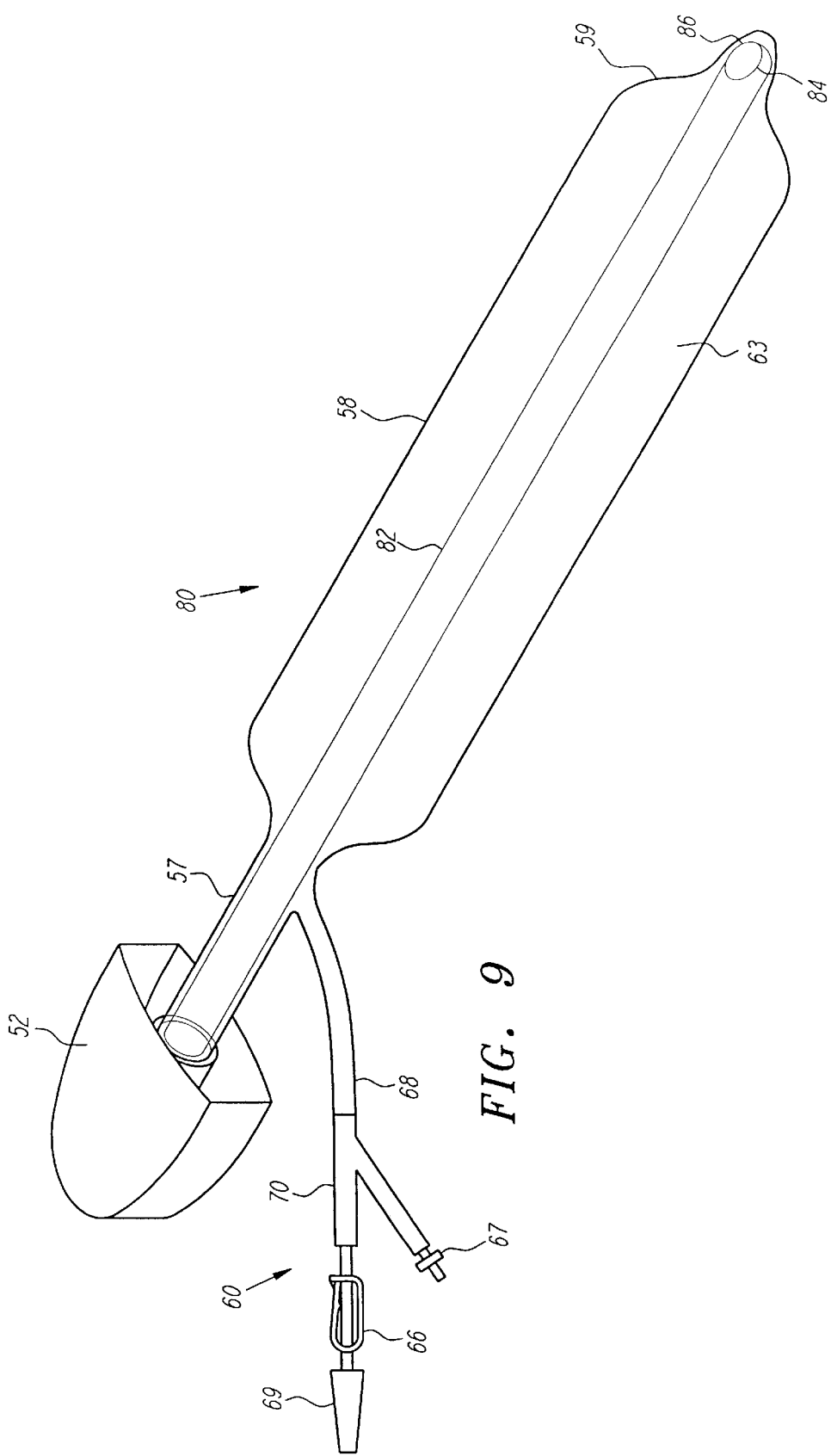
FIG. 9 is an isometric view of another embodiment of a balloon dissector according to the invention with visualization capability illustrated in its expanded state.

Another embodiment of a balloon dissector 80 is illustrated in FIG. 9. The balloon dissector 80 differs from the balloon dissector 50 only in that the tubular member 82 replaces the tunneling shaft 54 and an opening in communication with the bore in the tubular member 82 is provided in the handle 52. In this embodiment, the tubular member 82 serves as a scope cover to provide the dissector 80 with visualization capability when used in conjunction with a laparoscope. The tubular member 82 has an internal diameter, such as 10 mm for example, sized to receive a conventional laparoscope. The tubular member 80 may be formed of any suitable material, such as plastic for example.

The tubular member 82 may have an open distal end 84 as illustrated in FIG. 9 to permit observation with the laparoscope through the open distal end 84. As shown in FIG. 9, the open distal end 84 of the tubular member 82 may be cut away at a 45 degree angle, for example, and provided with a lip 86 which serves to capture the distal end of the laparoscope when inserted to prevent the laparoscope from extending beyond the open distal end 84. Alternatively, the open distal end 84 of the tubular member 82 may be squared off and the lip 86 provided by rolling the open distal end inward. The distal end of the tubular member 82 may also be closed and rounded if visualization through an open distal end is not desired.

An instrument seal, which may comprise an area of reduced internal diameter in the tubular member 82, may be provided to prevent the balloon inflation fluid from leaking out of the handle 52 during balloon inflation. Alternatively, or in combination with the area of reduced diameter in the tubular member 82, an instrument seal of the type illustrated in application Ser. No. 08/570,766 may be provided in the handle 52.

In addition to the balloon inflation options described with regard to the FIGS. 7 and 8 embodiments, the elongate balloon 58 of the dissector 80 may be inflated by injecting the inflation fluid through an inflation port in the handle 52 directly into a lumen in the tubular member 82. If the tubular member 82 has the presently preferred open distal end construction, the inflation fluid may be communicated through the bore in the tubular member 82 and out the open distal end 84 into the interior space 63 of the balloon 58. If a closed-ended tubular member 82 is utilized, inflation may be through a separate lumen formed in the wall of the tubular member 82 which opens into the interior space 63 of the balloon 58.

To prepare for tunneling dissection, a laparoscope, which may be a conventional 10 mm laparoscope, for example, is inserted through the handle 52 and advanced into the bore of the tubular member 82 until the distal extremity of the laparoscope is captured by the lip 86 in the open distal end 84 of the tubular member 82. The lip 86 in the open distal end 84 thus prevents the laparoscope from being advanced beyond the open distal end of the tubular member 82. Although an angled scope will provide the best visualization through the open distal end 84 of the tubular member 82, a straight scope may also be utilized.

The balloon dissector 80 is then inserted through the incision and tunneled bluntly following the desired tissue planes using the laparoscope and tubular member 82 as a blunt obturator. The procedure to be followed is the same as previously described with regard to the FIG. 7 and 8 embodiments with the exception that the progress of the operation may be observed through the laparoscope during tunneling dissection. During the tunneling stage, the distal end of the laparoscope looks out through the open distal end 84 of the tubular member 82 obstructed by only a single and preferably transparent layer of the elongate balloon 58. Moreover, when the balloon 58 is inflated to create a tunnel alongside the desired elongate structure, the laparoscope may be utilized to observe the progress of the dissection.

Figure 10:
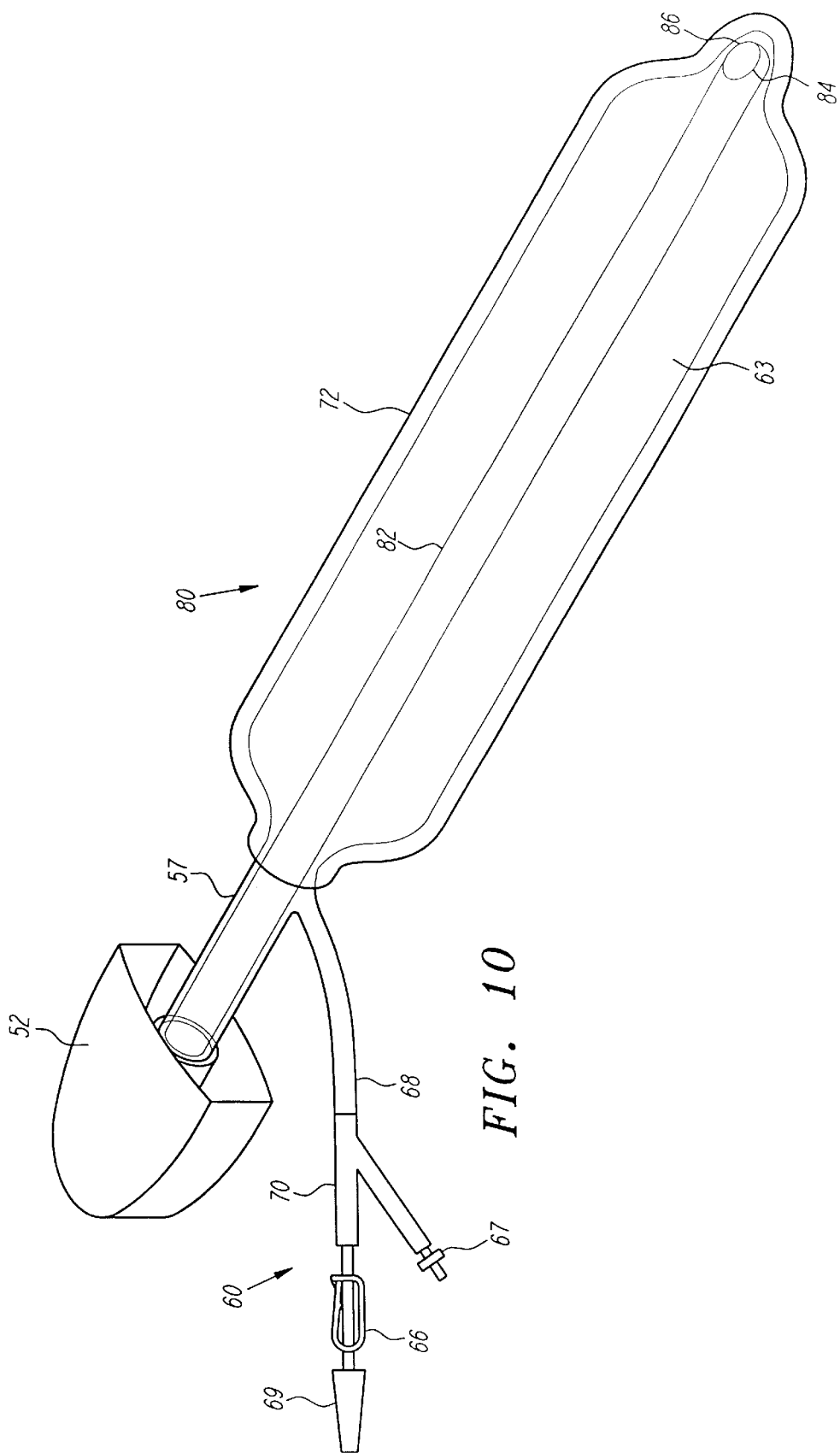
FIG. 10 is a view of the balloon dissector illustrated in FIG. 9 with a resilient balloon cover surrounding the elongate balloon.

FIG. 10 illustrates the addition of a resilient cover 72 to the balloon dissector 80 having visualization capabilities. The cover 72 may be of the same construction as previously described and may function in an equivalent manner to automatically compress the elongate balloon 58 about the tubular member 82 upon deflation.

The balloon loaded devices disclosed herein can be used in other procedures besides dissection for vein harvesting. The description of the devices in that environment is intended to be illustrative of the device only. It is readily apparent that the devices and methods may be used for tunneling and enlarging working spaces over other long structures in the body. Various arteries and veins must be exposed and mobilized for other operations, such as popliteal bypass, or a dialysis vein loop. In these operations, a vein must be harvested, and the sites at which the vein will be attached or anastomosed must also be uncovered. The balloon loaded devices may also be used to gain access to any blood vessel for any type of vascular surgery. For example, communicating veins or perforators in the calf may be exposed by dissecting the muscles deep within the calf to expose these blood vessels to accomplish a Linton procedure laparoscopically. The devices and methods may be used to expose those portions of the arteries to which grafts will be placed.

Other vessels may be dissected from surrounding tissue, such as fallopian tubes, spermatic cords, bile ducts, intestines and others. These vessels may be dissected and mobilized laparoscopically using the devices and techniques described above. Embodiments of the device may also be used to retrofit a scope with a balloon dissector to dissect a tunnel under direct vision. Alternatively, the balloon can be used to guide or support a scope within an existing space that needs periodic dilation to permit advancement of the scope. For example, a colonoscope may be fitted with one of the balloon devices disclosed herein and the device used to facilitate insertion of the colonoscope into the colon, especially around the splenic flexure, by inflating the balloon when the tip of the colonoscope approaches the splenic flexure. A urethral scope may be fitted with the devices disclosed herein to facilitate insertion of the scope into the urethra, which often requires dilation before insertion of a scope. The disclosed devices may be used in combination with a scope as an anchor, which while inflated serves to hold the scope in place within the body. While the preferred embodiments of the devices and methods have been described, they are merely illustrative of the principles of the invention. Other embodiments and configurations may be devised without departing from the spirit of the inventions and the scope of the appended claims.

What is claimed is:

1. A surgical apparatus comprising:

an elongate shaft having proximal and distal ends, said elongate shaft having sufficient rigidity to push through body tissue free of naturally occurring openings in the body tissue alongside an elongate structure;

an elongate balloon capable of assuming deflated and inflated states on said elongate shaft, said elongate balloon having an axial length substantially greater than a transverse diameter of said elongate balloon when said elongate balloon is in said inflated state, said balloon defining an inflatable interior space into which a fluid is introduced to inflate said balloon;

said distal end of said elongate shaft located inside said inflatable interior space; and a fluid passageway in communication with said inflatable interior space in said elongate balloon for communicating an inflation fluid to said elongate balloon.

2. The device of claim 1 wherein said elongate shaft is at least partly flexible.

3. The device of claim 1 further comprising a balloon cover surrounding said elongate balloon.

4. The device of claim 3 wherein said balloon cover is formed from a resilient material having sufficient elasticity to collapse said elongate balloon about said shaft when said elongate balloon is deflated.

5. The device of claim 4 wherein said resilient cover comprises a second elongate balloon that may be inflated independently of said elongate balloon.

6. The device of claim 3 wherein said balloon cover is a semi-rigid tubular member and is removable from said elongate balloon.

7. The device of claim 3 wherein said balloon cover is attached to said elongate balloon and separates to release said elongate balloon upon expansion of said elongate balloon.

8. The device of claim 1 wherein said elongate shaft is a tubular member having a lumen therein for receiving a surgical instrument.

9. The device of claim 1 wherein said elongate balloon extends from said proximal end of said shaft to said distal end of said shaft.

10. A pushable balloon dissection apparatus comprising:

a tubular member having proximal and distal ends, said tubular member having sufficient rigidity to push through body tissue free of naturally occurring openings alongside an elongate structure;

an elongate balloon capable of assuming deflated and inflated states on said tubular member, said elongate balloon having an axial length substantially greater than a transverse diameter of said elongate balloon when said elongate balloon is in said inflated state, said balloon defining an inflatable interior space into which a fluid is introduced to inflate said balloon;

said distal end of said tubular member located in said inflatable interior space; and an inflation port in communication with said inflatable interior space.

11. The device of claim 10 further comprising a balloon cover surrounding said elongate balloon.

12. The device of claim 10 wherein said balloon cover is formed from a resilient material having sufficient elasticity to collapse said elongate balloon about said tubular member when said elongate balloon is deflated.

13. The device of claim 11 wherein said balloon cover comprises a second elongate balloon that may be inflated independently of said elongate balloon.

14. The device of claim 10 wherein said balloon cover is a semi-rigid tubular member and is removable from said elongate balloon.

15. The device of claim 10 wherein said balloon cover is attached to said elongate balloon and separates to release said elongate balloon upon expansion of said elongate balloon.

16. The device of claim 10 wherein said tubular member has an internal bore sized to receive a surgical instrument and an open distal end.

17. The device of claim 16 wherein said surgical instrument is a scope.

18. The device of claim 16 wherein said open distal end has a lip partially blocking said internal bore.

19. The device of claim 10 wherein said elongate balloon is formed from an elastic material and said balloon cover is formed from an inelastic material.

20. The device of claim 10 wherein said elongate balloon extends from said proximal end of said tubular member to said distal end of said tubular member.

* * * * *

UNITED STATES PATENT AND TRADEMARK OFFICE
CERTIFICATE OF CORRECTION

PATENT NO.   : 5,944,734
DATED        : August 31, 1999
INVENTOR(S)  : George D. Hermann et al.

It is certified that error appears in the above-identified patent and that said Letters Patent is hereby corrected as shown below:

Column 2,
Line 60, please change "or" to -- of --.

Column 4,
Line 24, please change "injects" to -- inject --.

Column 5,
Line 20, please change "of" to -- for --.
Line 62, please change "16" to -- 27 --.

Column 10,
Line 29, please change "80" to -- 82 --.

Signed and Sealed this

Second Day of July, 2002

*Attest:*

JAMES E. ROGAN
*Director of the United States Patent and Trademark Office*

*Attesting Officer*